US010863911B2

(12) United States Patent
Strahl et al.

(10) Patent No.: US 10,863,911 B2
(45) Date of Patent: Dec. 15, 2020

(54) DETECTING NEURONAL ACTION POTENTIALS USING A CONVOLUTIVE COMPOUND ACTION POTENTIAL MODEL

(71) Applicant: MED-EL Elektromedizinische Geraete GmbH, Innsbruck (AT)

(72) Inventors: Stefan Strahl, Göttingen (DE); Konrad Eugen Schwarz, Axams (AT); Angelika Dierker, Innsbruck (AT); Philipp Spitzer, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 319 days.

(21) Appl. No.: 15/892,651

(22) Filed: Feb. 9, 2018

(65) Prior Publication Data
US 2018/0160924 A1   Jun. 14, 2018

Related U.S. Application Data

(63) Continuation of application No. 14/576,804, filed on Dec. 19, 2014, now abandoned.
(Continued)

(51) Int. Cl.
*A61B 5/04* (2006.01)
*A61N 1/36* (2006.01)
(Continued)

(52) U.S. Cl.
CPC ........ *A61B 5/04001* (2013.01); *A61B 5/0031* (2013.01); *A61B 5/125* (2013.01);
(Continued)

(58) Field of Classification Search
CPC .. A61N 1/0541; A61N 1/36036–36039; A61B 5/04001; A61B 5/6815–6817; A61B 5/4041–4052
See application file for complete search history.

(56) References Cited

U.S. PATENT DOCUMENTS 6,205,360 B1   3/2001   Carter et al.
7,150,710 B2   12/2006  Haber et al.
(Continued)

FOREIGN PATENT DOCUMENTS

CN   101751921       6/2010
CN   102908150 A     2/2013

OTHER PUBLICATIONS

International Searching Authority, International Search Report—International Application No. PCT/US2014/071425, dated Mar. 19, 2015 together with the Written Opinion of the International Searching Authority, 20 pages.
(Continued)

*Primary Examiner* — Thaddeus B Cox
(74) *Attorney, Agent, or Firm* — Sunstein LLP

(57) ABSTRACT

A hearing implant fitting system includes a physiological database containing physiological data characterizing auditory neural tissue response to electrical stimulation. A neural action potential (NAP) measurement system measures NAP signals from cochlear tissue responding to electrical stimulation signals delivered by one or more of the electrode contacts, including: deriving a compound discharge latency distribution (CDLD) of the cochlear tissue by deconvolving: (1) a tissue response measurement signal taken responsive to the delivered electrical stimulation signals, with (2) an elementary unit response signal representing voltage change at a measurement electrode contact due to the electrical stimulation, and then comparing the CDLD to physiological data from the physiological database to detect an NAP signal from the tissue response measurement signal. A fitting display provides to the fitting audiologist a visual display representing the CDLD and the NAP signal for fitting the electrode array to an implanted patient.

9 Claims, 8 Drawing Sheets
(3 of 8 Drawing Sheet(s) Filed in Color)

Related U.S. Application Data

(60) Provisional application No. 61/918,915, filed on Dec. 20, 2013.

(51) Int. Cl.
*A61N 1/05* (2006.01)
*A61B 5/00* (2006.01)
*G06N 7/00* (2006.01)
*A61B 5/12* (2006.01)

(52) U.S. Cl.
CPC .......... *A61B 5/4041* (2013.01); *A61B 5/6817* (2013.01); *A61B 5/7257* (2013.01); *A61N 1/36039* (2017.08); *G06N 7/005* (2013.01); *A61N 1/0541* (2013.01)

(56) References Cited

U.S. PATENT DOCUMENTS

| | | | |
|---|---|---|---|
| 8,180,440 | B2 | 5/2012 | McCombie et al. |
| 2005/0216072 | A1 | 9/2005 | Mahadevan-Jansen et al. |
| 2010/0069996 | A1 | 3/2010 | Strahl |
| 2010/0114190 | A1 | 5/2010 | Bendett et al. |
| 2010/0168603 | A1 | 7/2010 | Himes et al. |
| 2012/0203079 | A1 | 8/2012 | McLaughlin |
| 2013/0023967 | A1 | 1/2013 | Stafford et al. |

OTHER PUBLICATIONS

References: AJ.
Idrick Akhoun et al., *Electrically evoked compound action potential artifact analysis: Technique validation*, Hearing Research, Elsevier Science Publishers, Amsterdam, NL, vol. 302, Apr. 28, 2013, pp. 60-73.
R. Charlet de Sauvage et al., *Mathematical analysis of VIIIth nerve cap with a linearly-fitted experimental unit response*, Hearing Research, Elsevier Science Publishers, Amsterdam, NL, vol. 29, No. 2-3, Jan. 1, 1987, pp. 105-115.
Huib Versnel et al., *Single-fibre and whole-nerve responses to clicks as a function of sound intensity in the guinea pig*, Hearing Research, Elsevier Science Publishers, Amsterdam, NL, vol. 59, No. 2, May 1, 1992, pp. 138-156.
European Patent Office, Extended European Search Report, Application No. 14872689.6, dated Sep. 5, 2017, 11 pages.

DETECTING NEURONAL ACTION POTENTIALS USING A CONVOLUTIVE COMPOUND ACTION POTENTIAL MODEL This application is a continuation of U.S. patent application Ser. No. 14/576,804, filed Dec. 19, 2014, now abandoned, which in turn claims priority from U.S. Provisional Patent Application 61/918,915, filed Dec. 20, 2013, both of which are incorporated herein by reference in their entireties.

TECHNICAL FIELD

The present invention relates to detecting neuronal action potential signals from tissue responding to electrical stimulation signals, especially for hearing implant systems such as cochlear implant systems.

BACKGROUND ART

Most sounds are transmitted in a normal ear as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolus where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is associated with the cochlea 104, a cochlear implant with an implanted stimulation electrode can electrically stimulate auditory nerve tissue with small currents delivered by multiple electrode contacts distributed along the electrode.

In some cases, hearing impairment can be addressed by a cochlear implant (CI), a brainstem-, midbrain- or cortical implant that electrically stimulates auditory nerve tissue with small currents delivered by multiple electrode contacts distributed along an implant electrode. For cochlear implants, the electrode array is inserted into the cochlea. For brainstem, midbrain and cortical implants, the electrode array is located in the auditory brainstem, midbrain or cortex, respectively.

FIG. 1 shows some components of a typical cochlear implant system where an external microphone provides an audio signal input to an external signal processor 111 which implements one of various known signal processing schemes. For example, signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, fine structure processing (FSP) and compressed analog (CA) signal processing.

The processed signal is converted by the external signal processor 111 into a digital data format, such as a sequence of data frames, for transmission by an external coil 107 into a receiving stimulator processor 108. Besides extracting the audio information, the receiver processor in the stimulator processor 108 may perform additional signal processing such as error correction, pulse formation, etc., and produces a stimulation pattern (based on the extracted audio information) that is sent through electrode lead 109 to an implanted electrode array 110. Typically, the electrode array 110 includes multiple stimulation contacts 112 on its surface that provide selective electrical stimulation of the cochlea 104.

To collect information about the electrode—nerve interface, a commonly used objective measurement is based on the measurement of Neural Action Potentials (NAPs) such as the electrically-evoked Compound Action Potential (eCAP), as described by Gantz et al., *Intraoperative Measures of Electrically Evoked Auditory Nerve Compound Action Potentials*, American Journal of Otology 15 (2):137-144 (1994), which is incorporated herein by reference. In this approach, the recording electrode is usually placed at the scala tympani of the inner ear. The overall response of the auditory nerve to an electrical stimulus is measured typically very close to the position of the nerve excitation. This neural response is caused by the super-position of single neural responses at the outside of the auditory nerve membranes. The response is characterized by the amplitude between the minimum voltage (this peak is called typically N1) and the maximum voltage (peak is called typically P2). The amplitude of the eCAP at the measurement position is typically between 10 μV and 1800 μV. One eCAP recording paradigm is a so-called "amplitude growth function," as described by Brown et al., *Electrically Evoked Whole Nerve Action Potentials In Ineraid Cochlear Implant Users: Responses To Different Stimulating Electrode Configurations And Comparison To Psychophysical Responses*, Journal of Speech and Hearing Research, vol. 39:453-467 (June 1996), which is incorporated herein by reference. This function is the relation between the amplitude of the stimulation pulse and the peak-to-peak voltage of the eCAP. Another clinically used recording paradigm is the so called "recovery function" in which stimulation is achieved with two pulses with varying interpulse intervals. The recovery function as the relation of the amplitude of the second eCAP and the interpulse interval allows conclusions to be drawn about the refractory properties and particular properties concerning the time resolution of the auditory nerve.

Detecting NAPs such as eCAPs is based on an analysis of an obtained measurement recording (R) which can be understood as a signal mixture containing the desired NAPs (A), artifacts due to the stimulation (B) and other sources (C) and noise (D). The word "artifact", as used in this document refers to all signal components that are not caused by the eCAP response (except noise) and are usually unwanted and subject of removal. A linear model of this signal mixture is:

$$R = A + B + C + D$$

State-of-the-art NAP measurement systems apply special recording sequences to reduce the unwanted artifacts and the noise present during the measurement. The stimulation artifact (B) is partially removed from the recording (R) by different measurement paradigms such as "alternating stimulation" (Eisen M D, Franck K H: "Electrically Evoked Compound Action Potential Amplitude Growth Functions and HiResolution Programming Levels in Pediatric CII Implant Subjects." Ear & Hearing 2004, 25(6):528-538; which is incorporated herein by reference in its entirety), "masker probe" (Brown C, Abbas P, Gantz B: "Electrically evoked whole-nerve action potentials: data from human cochlear implant users." The Journal of the Acoustical Society of America 1990, 88(3):1385-1391; Miller C A, Abbas P J, Brown C J: An improved method of reducing stimulus artifact in the electrically evoked whole-nerve potential. Ear & Hearing 2000, 21(4):280-290; both of which are incorporated herein by reference in their entireties), "tri-phasic stimulation" (Zimmerling M: "Messung des elektrisch evozierten Summenaktionspotentials des Hörnervs bei Patienten mit einem Cochlea-Implantat." In PhD thesis Universität Innsbruck, Institut für Angewandte Physik; 1999; Schoesser H, Zierhofer C, Hochmair E S. "Measuring electrically evoked compound action potentials using triphasic pulses for the reduction of the residual stimulation artefact," In: Conference on implantable auditory prostheses; 2001; both of which are incorporated herein by reference in their entireties), and "scaled template" (Miller C A, Abbas P J, Rubinstein J T, Robinson B, Matsuoka A, Woodworth G: Electrically evoked compound action potentials of guinea pig and cat: responses to monopolar, monophasic stimulation. Hearing Research 1998, 119(1-2):142-154; which is incorporated herein by reference in its entirety). Artifacts due to other sources (C) are partially removed by a zero amplitude template (Brown et al. 2000). The noise (D) is reduced by repeated measurements, averaging over the repeated recordings reduces the noise level by $\sqrt{N}$ for N repetitions.

These special recording sequences result in a processed recording (R') with a reduced noise floor (D') and remaining artifacts (B' and C') which in most cases are reduced in amplitude. Some recording sequences also result in an altered NAP response (A'), for example the "masker probe" paradigm (Westen, A. A.; Dekker, D. M. T.; Briaire, J. J. & Frijns, J. H. M. "Stimulus level effects on neural excitation and eCAP amplitude." Hear Res, 2011, 280, 166-176; which is incorporated herein by reference in its entirety).

To automatically detect a NAP response in the resulting recording (R') one commonly used technique is known as template matching (SmartNRI as used by Advanced Bionics; Arnold, L. & Boyle, P. "SmartNRI: algorithm and mathematical basis." Proceedings of 8th EFAS Congress/10th Congress of the German Society of Audiology, 2007; which is incorporated herein by reference in its entirety). First an additional denoising of the recording (R') is performed by calculating correlations with basis functions predefined by a principal component analysis and performing weighted summation, resulting in a recording (R") with reduced noise (see U.S. Pat. No. 7,447,549; which is incorporated herein by reference in its entirety). Then an artifact model ($B_{Model}$+ $C_{Model}$) representing the sum of two decaying exponentials is fitted to this post-processed recording (R") and with a strength of response metric (SOR=(R"−$B_{Model}$−$C_{Model}$)/ noise) a threshold is determined to detect a possible NAP (A) (U.S. Pat. No. 7,818,052; which is incorporated herein by reference in its entirety).

Another approach to automatically detect a NAP response in the resulting recording (R') is known as expert system (AutoNRT™ as used by Cochlear Ltd.; Botros, A.; van Dijk, B. & Killian, M. "AutoNRT™: An automated system that measures ECAP thresholds with the Nucleus® Freedom™ cochlear implant via machine intelligence" Artificial Intelligence in Medicine, 2007, 40, 15-28; which is incorporated herein by reference in its entirety). The expert system used is a combination of a template matching and a decision tree classifier (U.S. Patent Publication US 20080319508 A1; which is incorporated herein by reference in its entirety). The template matching classifier computes the correlation with a NAP (A) template and a NAP plus stimulation artifact (A+B) template. The decision tree uses the following six parameters:

N1-P1 amplitude for NAP typically latencies
noise level
ratio N1-P1 amplitude to noise level
correlation with NAP (A) template
correlation with NAP plus stimulation artifact (A+B) template
correlation between this measurement (R) and a previous measurement at a lower stimulation amplitude.

Two different decision tree classifiers were learned with a C5.0 decision tree algorithm. For the case where no NAP (A) was detected at lower stimulation levels, the stimulation level was increased and a decision tree with a low false positive rate was used to determine the presence of a NAP (A). For the case where a NAP (A) was detected, the stimulation level was reduced and a decision tree with a low overall error rate was used to evaluate the presence of a NAP (A).

SUMMARY

Embodiments of the present invention are directed to a hearing implant fitting system that is configured for use by a fitting audiologist to fit an electrode array implanted in a patient cochlea and having electrode contacts for electrically stimulating adjacent neural tissue for perception as sound. A physiological database contains physiological data characterizing auditory neural tissue response to electrical stimulation. And a neural action potential (NAP) measurement system including a hardware-implemented processor executes software instructions for measuring NAP signals from cochlear tissue responding to electrical stimulation signals delivered by one or more of the electrode contacts, wherein measuring NAP signals includes: deriving a compound discharge latency distribution (CDLD) of the cochlear tissue by deconvolving: (1) a tissue response measurement signal taken responsive to the delivered electrical stimulation signals, with (2) an elementary unit response signal representing voltage change at a measurement electrode contact due to the electrical stimulation, and then comparing the CDLD to physiological data from the physiological database to detect an NAP signal from the tissue response measurement signal. A fitting display is configured for providing to the fitting audiologist a visual display representing the CDLD and the NAP signal for fitting the electrode array to an implanted patient.

The physiological data may be characterized by a plurality of Gaussian Mixture Models (GMM) such as two-component GMM. The derivation of the GMMs parameters may use a least mean square fitting. And the GMMs may include parameter distributions as a function of one or more of stimulation amplitude, inter-pulse interval during a recovery sequence, masker and stimulation level during a recovery sequence, stimulation pulse polarity, spatial distance between probe and masker electrodes during a spread of excitation sequence, and medical device generation, and the GMMs may include parameter distributions trained online by an expert to reflect a patient deviant parameter space. Comparing the CDLD to known physiological data may include comparing one or more of scale, latency and variation. A fast-Fourier transform algorithm may be used for the deconvolution. The NAP signal may be an electrically-evoked compound action potential (eCAP) signal.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
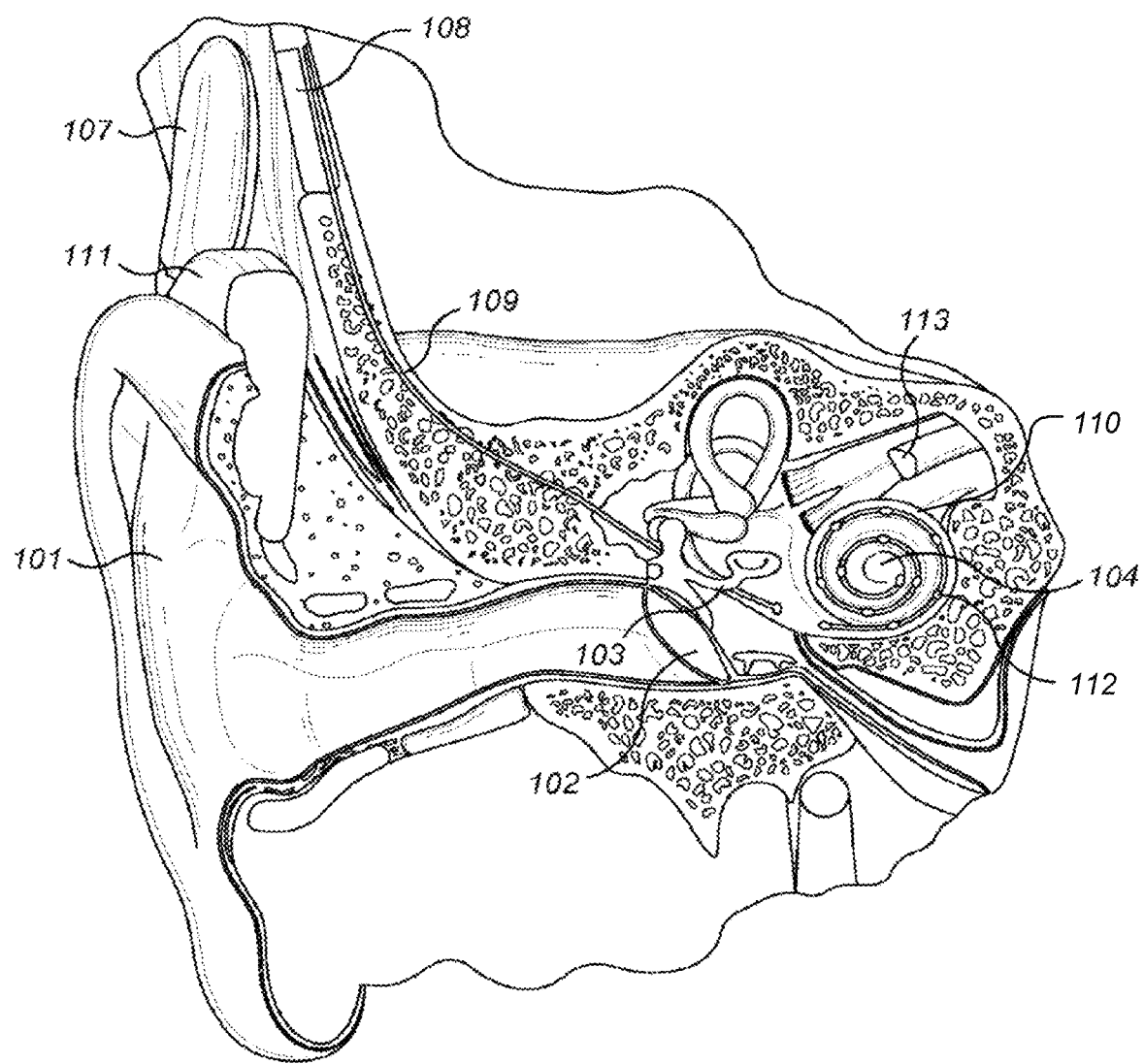
FIG. 1 shows anatomical structures of a human ear having a cochlear implant system.

Instead of using complex detection algorithms such as template matching or machine-learned expert systems such as decision tree classifiers to recognize possible NAPs directly in the tissue response measurement recording, embodiments of the present invention are directed to a signal processing system that deconvolves the tissue response measurement signal recording with a known elementary unit response to obtain a compound discharge latency distribution (CDLD). The CDLD is then examined to contain physiological properties which are assumed to have originated from NAPs such as an electrically-evoked compound action potential (eCAP) signal.

An NAP signal technically is a compound signal that represents the sum of a large number of synchronously occurring voltage changes due to electrically excited nerve fibers. The inventors found, that usage of a convolution model (see, e.g., Goldstein, M. H.; Kiang, N. Y. S. "Synchrony of neural activity in electric responses evoked by transient acoustic stimuli" JASA, Vol. 30, pp. 107-114 (1958); incorporated herein by reference in its entirety) to describe the NAP response x(t) using the following equation is suitable:

$$x(t) = N\int_{-\infty}^{t} P(\tau)U(t-\tau)d\tau \qquad \text{Eq. (1)}$$

where N represents the number of excited nerve fibers observable at the recording electrode, P(t) is the compound discharge latency distribution (CDLD) of the observable neural population, and U(t) is the voltage change at the electrode due to a single unit. Based on recordings in guinea pigs (see, e.g., Versnel, H.; Schoonhoven, R.; Prijs, V. F. "Single-fibre and whole-nerve responses to clicks as a function of sound intensity in the guinea pig" Hearing Research, Vol. 59, pp. 138-156 (1992); incorporated herein by reference in its entirety), the single unit response U(t) can be modeled by the following equations with for example $U_N$=0.12e-6 V, $\sigma_N$=0.12e-3 describing the negative part, and $U_P$=0.045e-6 V, $\sigma_P$=0.16e-3 describing the positive part, and $t_0$=−0.06e-3 s defines the cross point:

$$U(t) = \frac{U_N}{\sigma_N}(t-t_0)e^{\frac{1}{2}-\frac{(t-t_0)^2}{2\sigma_N^2}}, t < t_0 \qquad \text{Eq. (2a)}$$

$$U(t) = \frac{U_P}{\sigma_P}(t-t_0)e^{\frac{1}{2}-\frac{(t-t_0)^2}{2\sigma_P^2}}, t \geq t_0 \qquad \text{Eq. (2b)}$$

The CDLD P(t) defines how many nerve fibers discharge as a function of post-stimulus time and the inventors found that it can be modeled by a two-component Gaussian mixture model (GMM) as denoted in the following equation 3 with, for example, $\mu_1$=0.75e-3 s, $\sigma_1$=125e-6, $\mu_2$=1.50e-3 s and $\sigma_2$=1000e-6 and scale factor 3/2.

$$P(t) = \mathcal{N}(\mu_1, \sigma_1^2) + 3/2\, \mathcal{N}(\mu_2, \sigma_2^2) \qquad \text{Eq. (3)}$$

In a more general form the CDLD P(t) may be expressed by $$P(t) = (1-s) \times \mathcal{N}(\mu_1, \sigma_1^2) + s \times \mathcal{N}(\mu_2, \sigma_2^2)$$

Where $\mu_1$ and $\mu_2$ are the mean values, corresponding to the latency, and $\sigma_1$ and $\sigma_2$ the standard deviations of the first and second Gaussian component. The scale factor s describes the weighting of the two components to each other and completes the parameter-set. It is to be understood, that any other suitable GMM may be used as well.

Figure 2:
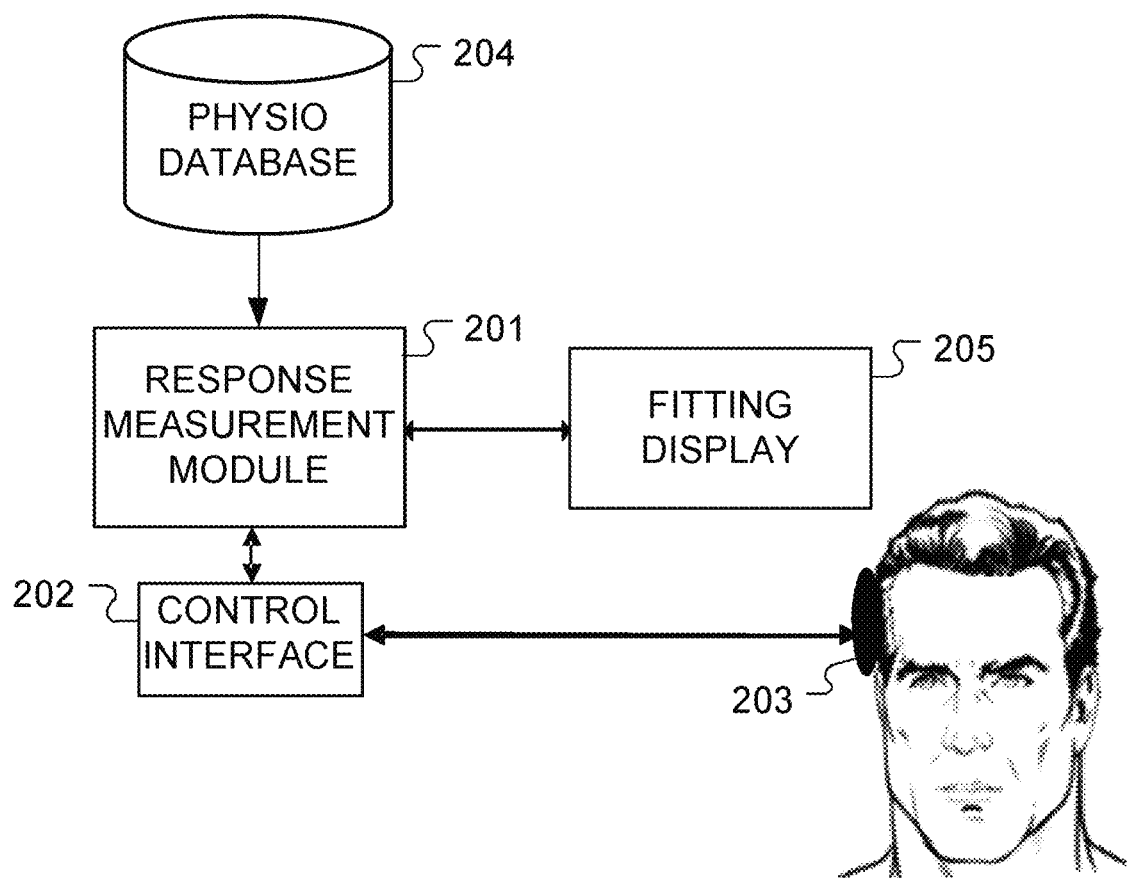
FIG. 2 shows various components in a system for measuring neural action potential (NAP) signals from tissue responding to electrical stimulation signals according to one specific embodiment of the present invention.

Based on the foregoing, embodiments of the present invention solve the inverse problem of Equation 1 for the tissue response measurement signal recording R to obtain the CDLD P(t), and analyze the resultant P(t) to recognize if an NAP signal is present. FIG. 2 shows various functional blocks in a system for measuring neural action potential (NAP) signals from tissue responding to electrical stimulation signals according to one specific embodiment of the present invention. Response measurement module 201 contains a combination of software and hardware for generating electrical stimulation pulses for the target neural tissue and recording and analyzing the NAPs. For example, the response measurement module 201 may be based on a Research Interface Box (RIB) II system manufactured at the University of Technology Innsbruck, Austria which may include a personal computer equipped with a National Instruments digital IO card, a RIB II isolation box, and a communications cable between IO card and RIB II box. The electrical stimulation pulses are transmitted from the response measurement module 201 through a control interface 202 to an external transmitter 203 which transmits them through the skin to implant electrodes to the target neural tissue. The NAP responses are recorded with the implant electrodes and transmitted by wire and/or wirelessly via the external transmitter 203, the control interface 202 to the response measurement module 201. It is understood, that any other way of communication between implant and control interface 202 or measurement module 201 may be equally possible. For example a direct wireless transmission from the implant to the control interface 202 as is for example advantageous for total implantable cochlear implants. Response measurement module 201 compares the measurement signals to known physiological data from Physio Database 204 as described below to detect NAPs such as eCAPs within the measurement signals.

Figure 3:
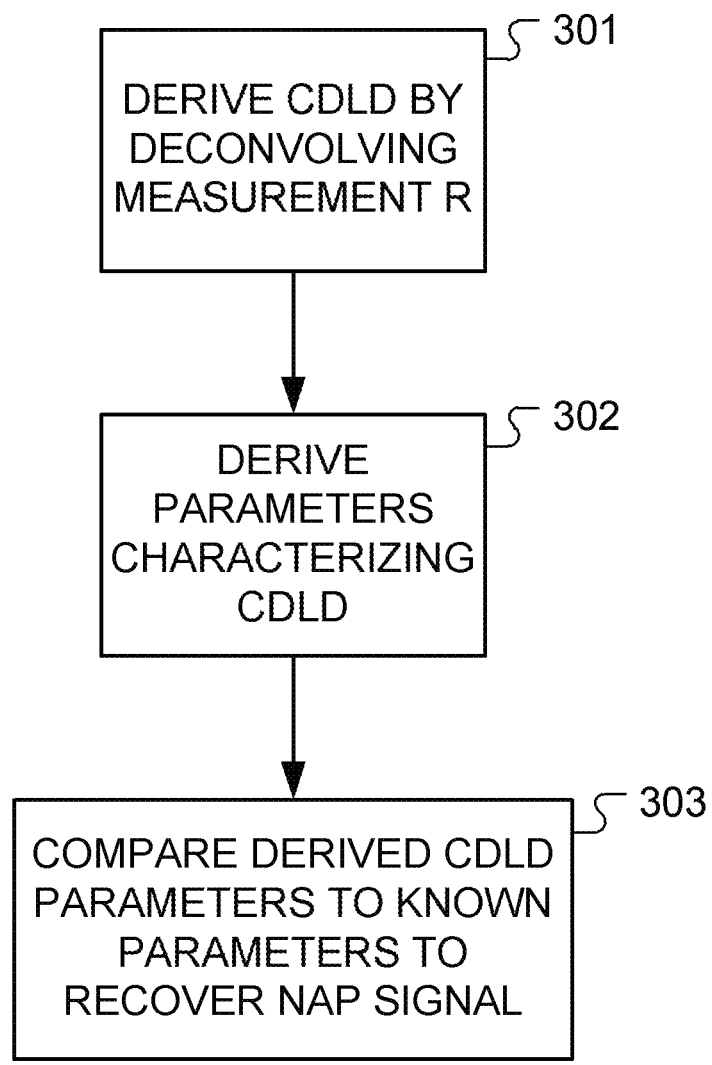
FIG. 3 shows the functional steps in a method of detecting neural action potential (NAP) signals from an obtained measurement recording (R) according to one specific embodiment of the present invention.
Figure 4:
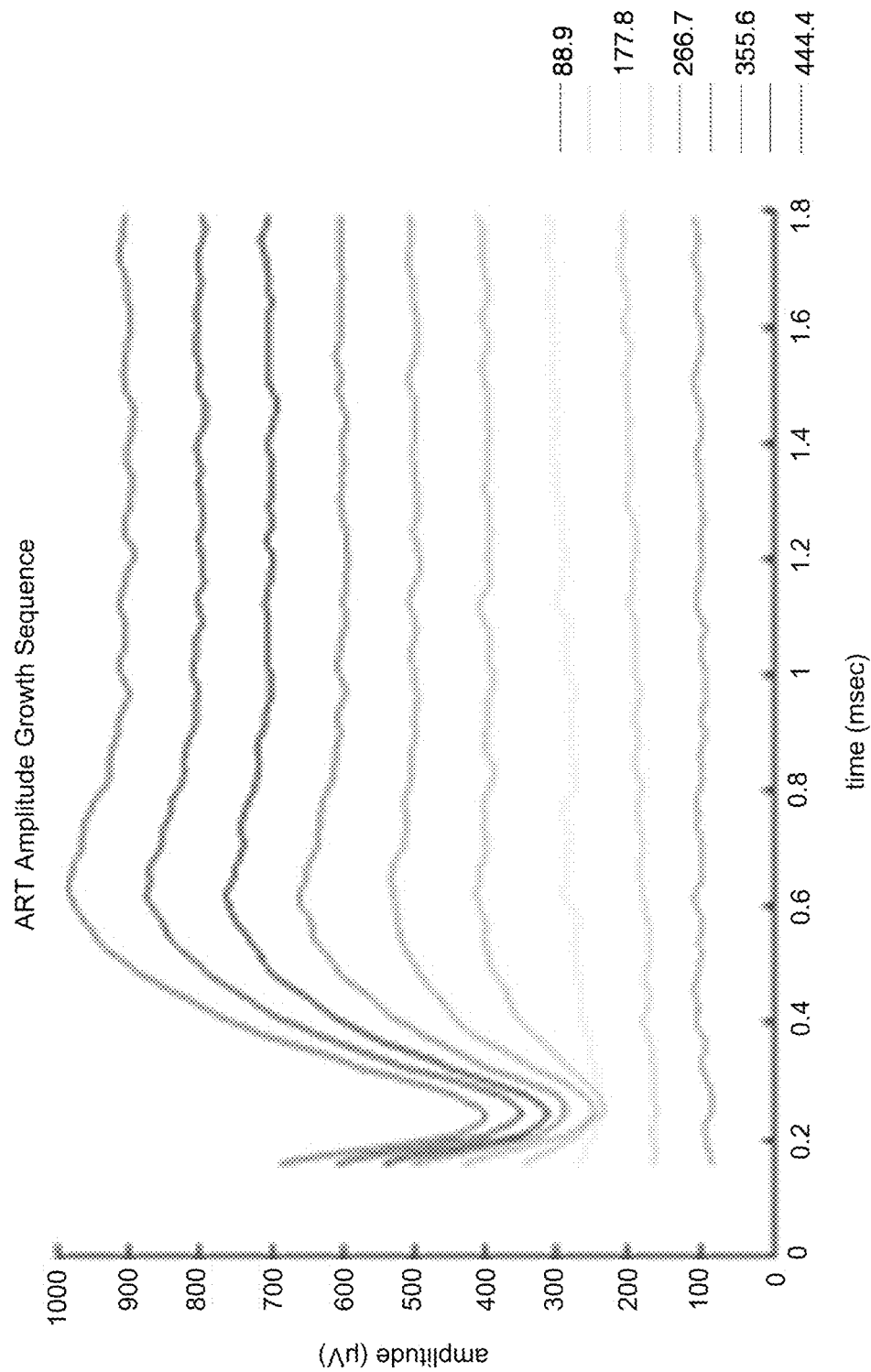
FIG. 4 shows examples of measurement recordings containing an NAP at higher stimulation levels.

FIG. 3 shows the functional steps in a method of detecting neural action potential (NAP) signals from neural tissue responding to electrical stimulation signals according to one specific embodiment of the present invention. First in step 301 the CDLD is derived by deconvolving the measurement R in response measurement module 201, then parameters are derived to characterize the CDLD in step 302. The derived parameters characterizing the CDLD are compared in step 303 using the Physio Database 204 with known parameters from physiological responses and if the recording R contains a CDLD with parameters within the physiological range a detected NAP is reported. FIG. 4 shows some examples of such measurement signal recordings R that contain an NAP at higher stimulation levels.

The response measurement module 201 derives a compound discharge latency distribution (CDLD) of the neural tissue by deconvolving the measurement signal with an elementary unit response signal (See FIG. 5) representing voltage change at the recording electrode due to the electrical stimulation of a nerve fiber, step 301. For example, a fast-Fourier transform may be used for this.

Figure 5:
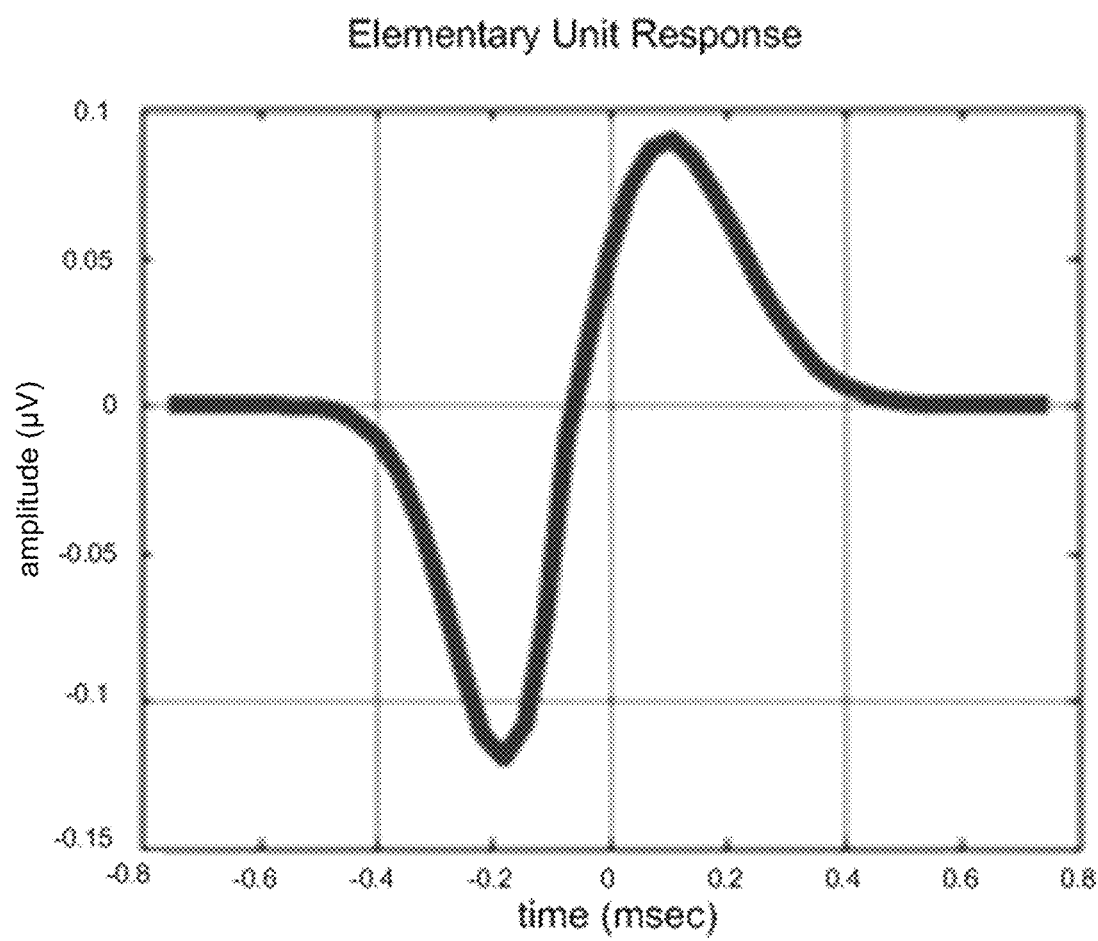
FIG. 5 shows an example of an elementary unit response.
Figure 6:
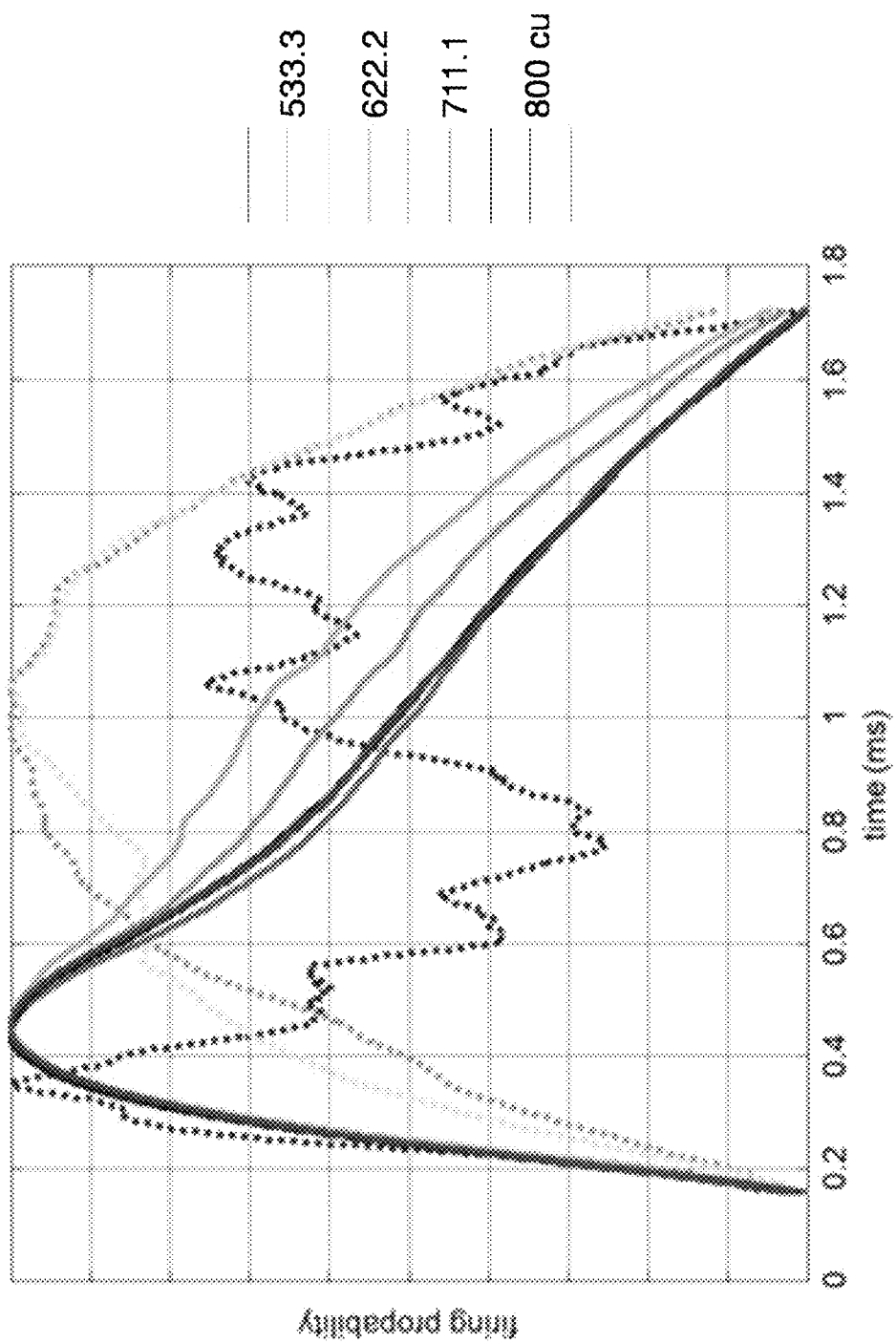
FIG. 6 shows a CDLD computed by deconvolving according to an embodiment of the present invention.

FIG. 6 shows a series of examples where the CDLD P(t) is computed by deconvolving the example measurement signals R from FIG. 4 with an elementary unit response U(t) as from FIG. 5. The example fitting display 205 of a CDLD shown in FIG. 6 also can usefully serve a visualization of the CDLD in a fitting software application for use by a fitting audiologist to allow the audiologist to easily see the characteristic shape of the response without having to delve into hard to understand values such as are often output from a complicated measurement and fitting algorithm. Such a fitting display 205 of a CDLD presents a nerve firing probability in an intuitive and helpful picture for audiologist.

Figure 7:
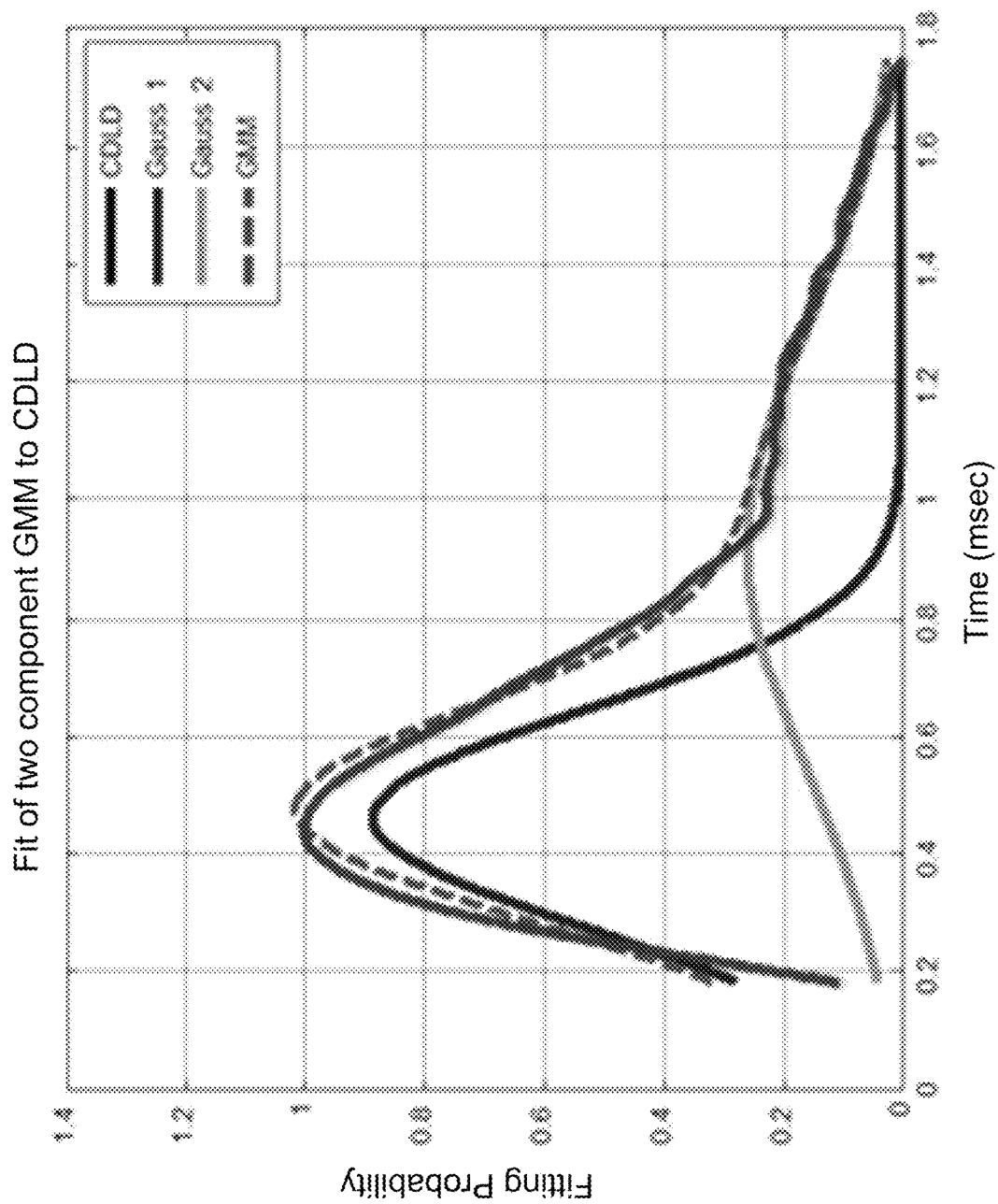
FIG. 7 shows a fitted two-component GMM.

The response measurement module 201 compares the CDLD to known physiological data from the Physio Database 204 to recover an NAP signal from the tissue response measurement signal R, step 303. For example, the physiological data in the Physio Database 204 may specifically include Gaussian mixture models (GMMs) such as two-component GMMs that the response measurement module 201 may fit to the CDLD using a least mean square algorithm. FIG. 7 shows an example of parameters of one such two-component GMM fitted to the CDLD.

Figure 8:
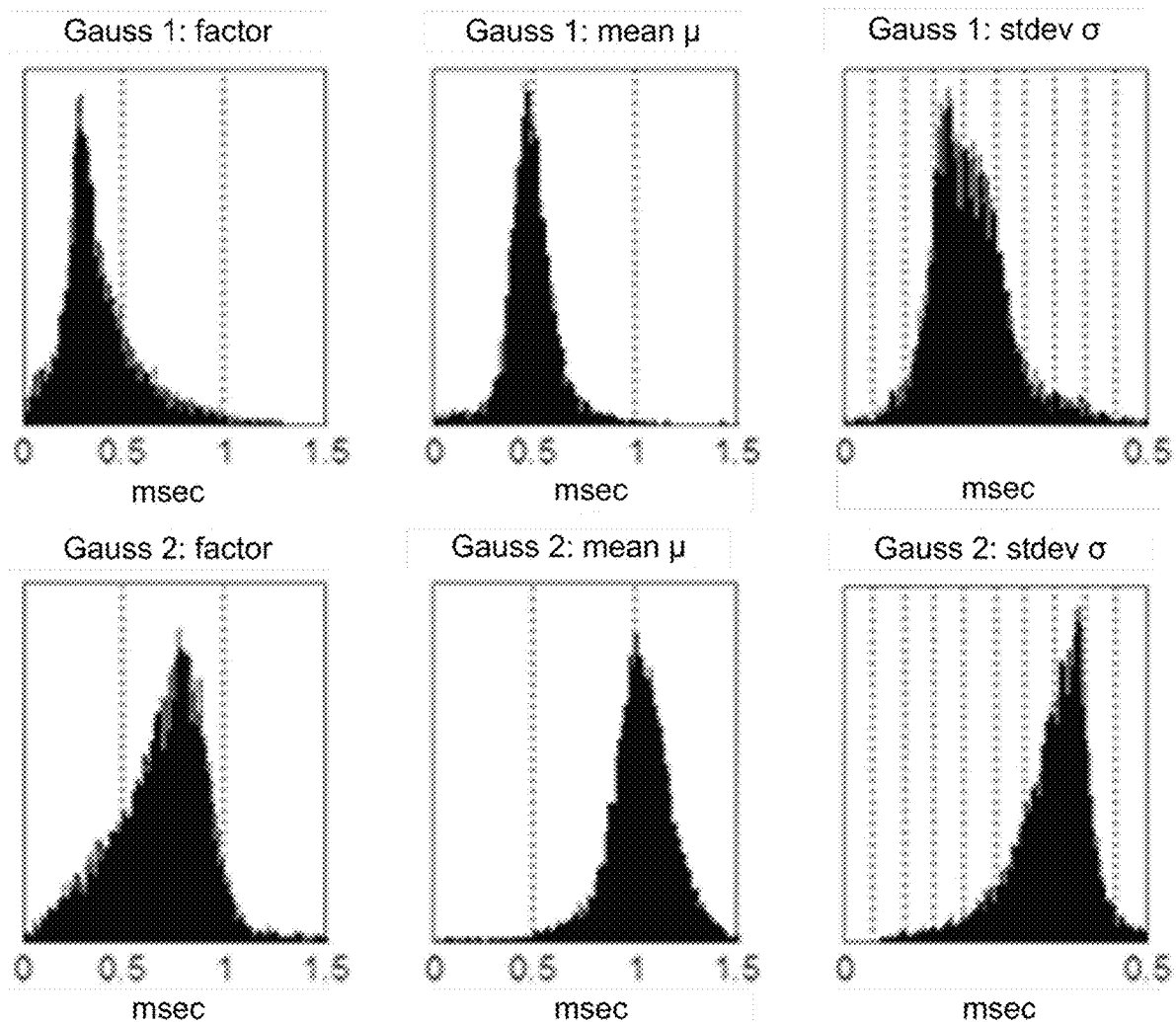
FIG. 8 shows distributions of fitted parameters of two-component GMM for physiological NAP responses.

When the derived parameters characterizing the CDLD are similar to examples stored in the Physio Database 204, the response measurement module 201 reports a detected NAP in the tissue response measurement signal, step 303. Some typical median values are shown in Table 1 and FIG. 8 shows some typical distributions of fitted parameters of two-component GMMs for physiological NAP responses that include scale factor, latency, and standard deviation.

TABLE 1

Median values for physiological NAP responses

| Gaussian Component | Scale Factor s | Latency $\mu$ | Standard Deviation $\sigma$ |
|---|---|---|---|
| 1. | 0.32 | 0.47 ms | 0.19 ms |
| 2. | 0.71 | 1.01 ms | 0.37 ms |

In specific embodiments, the parameter distributions of the fitted two-component GMMs in the GMM database 204 may be a function of one or more NAP recording parameters such as:
Stimulation amplitude
Inter-pulse interval during a recovery sequence
Masker and stimulation level during a recovery sequence
Polarity of stimulation pulse
Distance on electrode array between masker and probe during a spread of excitation sequence
Medical device generation And in some embodiments, the parameter distributions can be trained online by an expert to reflect a subject's deviant parameter space (like for speech recognition system that initially have a universal parameter distribution data which is then trained to local speaker with a training text).

Arrangements such as those described above provide low computational complexity resolution of NAPs from tissue response measurement signals based on physiological a priori knowledge of auditory nerve tissue.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments also can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A hearing implant fitting system configured for use by a fitting audiologist to fit an electrode array implanted in a patient cochlea and having a plurality of electrode contacts for electrically stimulating adjacent neural tissue for perception as sound, the system comprising:

a physiological database containing physiological data characterizing auditory neural tissue response to electrical stimulation; and a neural action potential (NAP) measurement system including a hardware-implemented processor executing software instructions for measuring NAP signals from cochlear tissue responding to electrical stimulation signals delivered by one or more of the electrode contacts, wherein measuring NAP signals includes:
i. deriving a compound discharge latency distribution (CDLD) of the cochlear tissue by deconvolving:
    (a) a tissue response measurement signal taken responsive to the delivered electrical stimulation signals, with
    (b) an elementary unit response signal representing voltage change at a measurement electrode contact due to the electrical stimulation;
ii. comparing the CDLD to physiological data from the physiological database to detect an NAP signal from the tissue response measurement signal; and a fitting display configured for providing to the fitting audiologist a visual display representing the CDLD and the NAP signal for fitting the electrode array to an implanted patient.

2. The system according to claim 1, wherein the physiological data is characterized by a plurality of Gaussian mixture models (GMMs).

3. The system according to claim 2, wherein the NAP measurement system is configured for comparing the CDLD to the GMM physiological data using a least mean square fitting.

4. The system according to claim 2, wherein the plurality of GMMs are two-component GMMs.

5. The system according to claim 2, wherein the plurality of GMMs include parameter distributions as a function of one or more of stimulation amplitude, inter-pulse interval during a recovery sequence, masker and stimulation level during a recovery sequence, stimulation pulse polarity, distance between a probe electrode and a masker electrode during a spread of excitation sequence, and medical device generation.

6. The system according to claim 2, wherein the plurality of GMMs include parameter distributions trained online by an expert to reflect a patient deviant parameter space.

7. The system according to claim 1, wherein the NAP measurement system is configured for comparing the CDLD to the physiological data based on using one or more of scale, latency and variation.

8. The system according to claim 1, wherein the NAP measurement system is configured for deconvolving by using a fast-Fourier transform algorithm.

9. The system according to claim 1, wherein the NAP signal is an electrically-evoked compound action potential (eCAP) signal.

* * * * *